(12) United States Patent
O'Mahony et al.

(10) Patent No.: US 7,303,540 B2
(45) Date of Patent: Dec. 4, 2007

(54) USER INTERFACE FOR BLOOD TREATMENT DEVICE

(75) Inventors: John J. O'Mahony, Minnetonka, MN (US); Thomas Robert Lendway, Vadnais Heights, MN (US); Andrew J. Halpert, Coral Springs, FL (US)

(73) Assignee: CHF Solutions, Inc., Brooklyn Park, MN (US)

( * ) Notice: Subject to any disclaimer, the term of this patent is extended or adjusted under 35 U.S.C. 154(b) by 433 days.

(21) Appl. No.: 10/831,292

(22) Filed: Apr. 26, 2004

(65) Prior Publication Data

US 2005/0256444 A1    Nov. 17, 2005

(51) Int. Cl.
*A61M 37/00* (2006.01)
*G06F 13/14* (2006.01)
*G06F 3/00* (2006.01)
*B01D 11/00* (2006.01)

(52) U.S. Cl. .................... 604/4.01; 210/645; 210/646; 210/647; 345/520; 715/700; 422/44; 604/5.01; 604/5.02; 604/6.01; 604/6.02

(58) Field of Classification Search ............... 604/4.01, 604/5.01–5.04, 6.01–6.04; 715/700; 345/520; 210/645–647; 422/44
See application file for complete search history.

(56) References Cited

U.S. PATENT DOCUMENTS

| | | | |
|---|---|---|---|
| 4,086,924 A | 5/1978 | Latham, Jr. | |
| 4,599,055 A | 7/1986 | Dykstra | |
| 4,657,529 A | 4/1987 | Prince et al. | |
| 4,784,768 A | 11/1988 | Mathieu | |
| 4,824,339 A | 4/1989 | Bainbridge et al. | |
| 4,936,980 A | 6/1990 | Yoshimichi et al. | |
| 5,114,580 A | 5/1992 | Ahmad et al. | |
| 5,312,550 A | 5/1994 | Hester | |
| 5,366,630 A | 11/1994 | Chevallet | |
| 5,487,827 A | 1/1996 | Peterson et al. | |
| 5,536,237 A | 7/1996 | Prince et al. | |
| 5,609,770 A * | 3/1997 | Zimmerman et al. | 210/739 |
| 5,653,887 A | 8/1997 | Wahl et al. | |
| 5,685,989 A | 11/1997 | Krivitski et al. | |
| 5,707,086 A | 1/1998 | Treu et al. | |
| 5,725,776 A | 3/1998 | Kenley et al. | |

(Continued)

FOREIGN PATENT DOCUMENTS

DE    26 44 062    9/1976

(Continued)

OTHER PUBLICATIONS

Strife, C.F. et al, "Experience With a Low Volume Ultrafiltration Cell in Small Children," Clinical Nephrology 8:410-413 (1977).

(Continued)

*Primary Examiner*—Tatyana Zalukaeva
*Assistant Examiner*—Ginger T. Chapman
(74) *Attorney, Agent, or Firm*—Nixon & Vanderhye P.C.

(57) ABSTRACT

A graphical user interface (GUI) for medical instruments for a Renal Replacement Therapy that enables an operator to select and review a series of settings for an extracorporeal pump console and implement the settings in batch manner. The GUI automatically adjusts or recommends dependent settings, e.g. filtration rate, as the user adjusts primary settings, e.g. blood flow rate.

13 Claims, 6 Drawing Sheets

U.S. PATENT DOCUMENTS

| | | | |
|---|---|---|---|
| 5,730,712 | A | 3/1998 | Falkvall et al. |
| 5,762,805 | A | 6/1998 | Truitt et al. |
| 5,776,345 | A | 7/1998 | Truitt et al. |
| 5,906,589 | A | 5/1999 | Gordon et al. |
| 5,910,252 | A | 6/1999 | Truitt et al. |
| 6,090,048 | A | 7/2000 | Hertz et al. |
| 6,146,523 | A | 11/2000 | Kenley et al. |
| 6,773,412 | B2 * | 8/2004 | O'Mahony et al. ........ 604/5.01 |
| 6,923,782 | B2 * | 8/2005 | O'Mahony et al. ........ 604/4.01 |
| 2001/0016699 | A1 | 8/2001 | Burbank et al. |
| 2001/0021817 | A1 | 9/2001 | Brugger et al. |
| 2001/0037079 | A1 | 11/2001 | Burbank et al. |
| 2001/0041892 | A1 | 11/2001 | Burbank et al. |
| 2002/0103453 | A1 | 8/2002 | Burbank et al. |
| 2002/0147423 | A1 | 10/2002 | Burbank et al. |
| 2003/0009123 | A1 | 1/2003 | Brugger et al. |
| 2003/0097087 | A1 | 5/2003 | Gura |
| 2003/0218623 | A1 * | 11/2003 | Krensky et al. ............ 345/700 |
| 2004/0084358 | A1 | 5/2004 | O'Mahony et al. |

FOREIGN PATENT DOCUMENTS

| | | |
|---|---|---|
| EP | 0 274 178 | 7/1988 |
| EP | 0 990 444 A2 | 4/2000 |
| GB | 1 583 023 | 1/1981 |
| WO | WO 02/082971 A3 | 10/2002 |

OTHER PUBLICATIONS

Lauer, A. et al, "Continuous Arteriovenous Hemofiltration in the Critically Ill Patient, Clinical Use and Operational Characteristics," Annals of Internal Medicine 99:455-460 (1983).

Verbanck, J. et al, "Pure Ultrafiltration by Repeated Puncture of a Peripheral Arm-Vein as Treatment of Refratory Edema", The International Journal of Artificial Organs, vol. 3, No. 6 (1980), pp. 342-343.

Silverstein et al, "Treatment of Severe Fluid Overload by Ultrafiltration," The New England Journal of Medicine, vol. 291, No. 15, Oct. 10, 1974, pp. 747-751.

Blake, P. et al, "Refractory Congestive Heart Failure: Overview and Application of Extracorporeal Ultrafiltration," Critical Care Nephrology, *Advances in Renal Replacement Therapy*, vol. 3, No. 2 (Apr. 1966), pp. 166-173.

Civati G. et al, "Haemofiltration Without Substitution Fluid," Proc. EDTA-ERA, vol. 21 (1984), pp. 441-446.

Jenkins, R.D. et al, "The Use of Continuous Arteriovenous Hemofiltration With Hemodialysis in a Newborn," Draft #6, Personal Communication, 1985 (6 pages).

Jacobs, C. et al, "Continuous Arteriovenous Hemofiltration," Replacement of Renal Function By Dialysis, 4$^{th}$ Ed., (1996) pp. 391-397.

Gupta, B.B. et al, "High Shear Rate Hemofiltration: Influence of Fiber Dimensions and Shear Rates," Artificial Organs, International Society for Artificial Organs, vol. 13(2) (1989), pp. 97-102.

Rimondini, A. et al, "Hemofiltration as Short-Term Treatment for Refractory Congestive Heart Failure," The American Journal of Medicine, vol. 83, Jul. 1987, pp. 43-48.

Donato, L. et al, "Treatment of End-Stage Congestive Heart Failure by Extracorporeal Ultrafiltration," The American Journal of Cardiology, vol. 59, (Feb. 1, 1987), pp. 379 and 380.

L'Abbate, A. et al, "Ultrafiltration: A Rational Treatment for Heart Failure," Cardiology 1989; 76:384-390.

Chen, Y. et al, "Direct Peripheral Venopuncture: Another New Choice of Temporary Vascular Access", Renal Failure, 22(3), 369-377 (2000).

Jonathan D. Sackner-Bernstein, MD et al., "How Should Diuretic-Refractory, Volume-Overloaded Heart Failure Patients Be Managed?" The Journal of Invasive Cardiology, vol. 15, No. 10 (Oct. 2003), pp. 585-590.

Brian E. Jaski, MD et al., "Peripherally Inserted Veno-Venous Ultrafiltration for Rapid Treatment of Volume Overloaded Patients", Journal of Cardiac Failure, vol. 9, No. 3, (Jun. 2003), pp. 227-231.

* cited by examiner

USER INTERFACE FOR BLOOD TREATMENT DEVICE

TECHNICAL FIELD

This invention relates to the medical instruments for extracorporeal treatment of blood and user interfaces for such instruments. One embodiment of the invention relates to a user interface for medical instruments for Renal Replacement Therapy and Artificial Kidney therapies.

BACKGROUND

1. Renal Replacement Therapies (RRT)

Renal Replacement Therapy (RRT) can be performed in specialized dialysis centers for treatment of chronic patients that have permanently lost kidney function and in hospitals for treatment of patients with a need for temporary replacement of renal function. Different modalities of Continuous Renal Replacement Therapy (CRRT) have been used to treat patients suffering from excess fluid overload and acute renal failure. In acute settings, CRRT has been performed using standard methods of hemodialysis and continuous arterio-venous hemofiltration (CAVH). More recently, continuous veno-venous hemofiltration (CVVH) has been used to reduce the complications associated with such issues as hemodynamic instability and need for arterial access. Regardless of the type of medical equipment used and the specific type of treatment performed, RRT requires establishing an extracorporeal blood circulation path that passes blood through a filtration device.

RRT performs two primary blood treatment functions: ultrafiltration (removal of water from blood plasma), and solute clearance (removal of different molecular weight substances from blood plasma). RRT involves the use of a filter in a blood circuit through which circulates extracorporeal blood temporarily withdrawn from a patient. The RRT filter, also called hemofilter or dialyzer, can be set up to perform either or both of these functions simultaneously, with or without fluid replacement, accounting for the various modes of renal replacement therapy. "Clearance" is a term that describes the removal of substances, both normal and waste product, from blood.

Ultrafiltration is the convective transfer of fluid out of a plasma compartment of a filter and through pores in the filter membrane. The pores of the filter membrane pass (filter) water, electrolytes and small and middle-sized molecules (up to 20,000 to 30,000 daltons) from the blood plasma. Large molecules, proteins blood cells and other large-sized plasma components (as well as a portion of the water and smaller components) do not pass through the filter membrane and remain in the plasma compartment of the blood circuit and are returned to the patient. The ultrafiltrate output (e.g., water extracted from the blood) from the filtration pores is similar to plasma, but without the plasma proteins or cellular components. Since the concentration of small solutes is the same in the ultrafiltrate as in the plasma, no clearance is obtained from the plasma, but fluid volume, e.g., water, is removed.

Dialysis is the diffusive transfer of small solutes out of a blood plasma compartment of a filter by diffusion across the filter membrane. This transfer occurs as a result of a concentration gradient, with diffusion occurring from the filter compartment with higher concentration (typically the blood compartment) to the filter compartment with lower concentration (typically the dialysate compartment). Since the concentration of solutes in the plasma decreases, clearance is obtained. Fluid may not be removed in dialysis. Ultrafiltration can be combined with dialysis to obtain both clearance and fluid removal from blood plasma.

Hemofiltration is the combination of ultrafiltration and fluid replacement in the treatment of blood. Typically, hemofiltration treats larger volumes of blood than is needed for fluid control alone. The replacement fluid added to blood during hemofiltration contains electrolytes, but not other small molecules. Since the net effect of replacing fluid without small solutes and ultrafiltration of fluid with small solutes results in net removal of small solutes, clearance is obtained during hemofiltration.

RRT devices typically use sets of disposable blood passage circuits (generally referred to as "disposables") generally including tubing, filters, catheters, sensors and connectors that form a fluid circuit and are in direct contact with the blood and the fluid removed from the blood. These disposables can be assembled from components made by various manufacturers. Some more expensive disposables such as dialyzers can be used several times to treat the same patient. In some cases, disposables come assembled and the user need only mount the disposable blood passage on an instrument and pumping machine, and then prime the blood passage with sterile saline solution prior to its use. When the RRT device is ready for use, it is connected to the network of disposable and fluid filled tubes and electronic sensors that include the disposable blood passageway.

2. Limitations of User Interface of Existing Devices for RRT

Modern RRT devices are microprocessor controlled. The microprocessor operates pumps, reads sensors and communicates with the user via a user interface regarding the RRT treatment. In advanced RRT devices, the user interface has a graphics display that may be a touch screen or have an associated keypad. By interacting with a display and keys, the user interface enables a user to control the RRT device and monitor its operation.

There is a long felt need for RRT devices that are operator friendly and fault tolerant. Simplifying the device setup and operation is helpful to minimizing training and reducing operator error. Implementing rules in software that can guide the user through the setup while not overly restricting the operating envelope of the device may be applied to improve the safety for patients and enhance the market adoption of the RRT device.

U.S. Pat. No. 5,858,239 discloses a dialysis machine that has a graphics display where a user is assisted by simple pictograms. A user interface that makes use of graphical icons is disclosed in U.S. Pat. No. 5,620,608 for a dialysis machine. These icons help a user of a dialysis device navigate through a menu system. A graphics user interface for an aphaeresis blood processing apparatus using pictorials is disclosed in U.S. Pat. No. 5,653,887, which displays icons and a symbolic diagram of the apparatus with an arrow pointing towards an element (blood centrifuge) requiring user attention. A graphical user interface for an RRT device is also disclosed in U.S. Patent Application Publication No. 2002/151804.

SUMMARY OF THE INVENTION

A new and improved graphical user interface (GUI) for a RRT (Renal Replacement Therapy) device has been developed that limits ultrafiltration rate based upon available blood flow rate and facilitates batch setting before setting implementation. The GUI is directed to an RRT device, but can be applied to other devices that involve extracorporeal circulation. Extracorporeal blood circulation involves the continuous withdrawal of blood from a patient, where the blood is processed outside of the patient and then returned to the patient. Examples of such treatments are blood aphaeresis, heart-lung machines, full or partial heart bypass and transfusion of blood.

The GUI addresses the needs of fluid removal and dialysis users by providing an intuitive interface that is algorithmically defined by a set of rules that defines the relationship between specific settings that enables adjustment of a single variable to affect the setting of other settings to accommodate predefined rules. The user may, if so desired, change the values of each of the control settings. When the user has changed all of the desired control settings, the changed values for each of the control settings may be accepted by touching an ACCEPT key. The values for the control is advantageous in that entry of multiple settings is easier and less time consuming. The affect of each setting change on other settings may be viewed in real time before they are actively enabled. Batch entry of operator settings is also useful in that all of the proposed values for the control settings of an RRT device are displayed, and may be checked for entry errors by the user before being enabled.

This invention may also be embodied as a user-friendly GUI in which dependent control settings are automatically adjusted as a user-operator manually adjusts independent control settings. Settings in an RRT type device may be mathematically related to each other such that changing one setting will have an effect on another. To avoid having the user-operator manually adjust both independent and dependent control settings, the GUI disclosed herein enables the user to adjust any of the possible settings in any sequence while enacting the functional limitation of the setting being changed upon all other related settings.

The invention may be embodied as a method for batch implementation of settings in a renal replacement therapy device comprising at least one fluid pump connectable to a detachable extracorporeal blood circuit, at least one pressure sensor monitoring pressuring in a blood line of the blood circuit, a controller regulating at least one fluid pump according to stored control settings and inputs for the at least one pressure sensor and a user interface, the method comprising: displaying on the user interface a plurality of control settings which may be manually selected by an operator; selecting an independent control setting of the plurality of control settings; adjusting the independent control setting to an independent control setting level selected by an operator; temporarily storing the adjusted independent control setting level, without first implementing the adjusted independent or dependent control setting levels to control the device; automatically adjusting a dependent control setting level based upon the independent control level, without implementing the adjusted dependent control setting level to control the device; displaying the adjusted independent control setting level and the adjusted dependent control setting, and implementing both the adjusted independent control setting level and the adjusted dependent control setting to control the device, by actuating a batch setting acceptance operation.

The invention may also be embodied as a method for batch implementation of settings in a renal replacement therapy device comprising at least one fluid pump connectable to a detachable extracorporeal blood circuit, at least one pressure sensor monitoring pressuring in a blood line of the blood circuit, a controller regulating at least one fluid pump according to stored control settings and inputs for the at least one pressure sensor and a user interface, the method comprising: displaying on the user interface a plurality of control settings which may be manually selected by an operator; selecting an independent control setting of the plurality of control settings; adjusting the independent control setting to an independent control setting level selected by an operator; temporarily storing the adjusted independent control setting level, without implementing the adjusted independent control setting level to control the device; automatically establishing a limit for a dependent control setting level based upon the adjusted independent control level, without first implementing the adjusted independent or dependent control setting levels to control the device; displaying a value for the dependent control setting level adjusting the dependent control setting level by an operator input, if the operator inputs a setting level within the limit for the dependent control setting level; issuing an alarm if the operator input of the dependent control setting level exceeds the established limit for the dependent control setting, and implementing both the adjusted independent control setting level and the adjusted dependent control setting to control the device, by actuating a batch setting acceptance operation.

The invention may also be further embodied as a method for batch implementation of settings in a renal replacement therapy device comprising at least one fluid pump connectable to a detachable extracorporeal blood circuit, at least one pressure sensor monitoring pressure in a blood line of the blood circuit, a controller regulating the at least one fluid pump according to stored control settings and inputs for the at least one pressure sensor and a user interface, said method comprising: displaying on the user interface a plurality of control settings which may be manually selected by an operator; selecting a first independent control setting of the plurality of control settings; adjusting the first independent control setting to a first independent control setting level selected by an operator; temporarily storing the first independent control setting level, without implementing the first independent control setting level to control the device; automatically establishing a limit for a first dependent control setting level based upon the first independent control level, without first implementing the first independent or dependent control setting levels to control the device; selecting the first dependent control level for manual adjustment, wherein the selection converts the first dependent control setting to a second independent control setting and converts the first independent control setting to a second dependent control setting; adjusting the second independent control setting to an second independent control setting level selected by an operator; temporarily storing the second independent control setting level, without implementing the second independent control setting level to control the device; automatically establishing a limit for the second dependent control setting level based upon the first independent control level, without first implementing the second independent control setting level or the second dependent control setting levels to control the device, and implementing both the second independent control setting level and the second dependent control setting level to control the device by actuating a batch setting acceptance operation.

The invention may be further embodied as a method for batch implementation of settings in a renal replacement therapy device comprising at least one fluid pump connectable to a detachable extracorporeal blood circuit, at least one pressure sensor monitoring pressuring in a blood line of the blood circuit, a controller regulating the at least one fluid pump according to stored control settings and inputs for the at least one pressure sensor and a user interface, said method comprising: displaying on the user interface a plurality of control settings which may be manually selected by an operator; selecting a control setting of the plurality of control settings, wherein the selection of the control setting establishes the selected setting as an independent control setting; adjusting the independent control setting to an independent control setting level selected by the operator; temporarily storing the adjusted independent control setting level without first implementing the control setting levels to control the device; automatically adjusting at least one dependent control setting level based upon the independent control level and without implementing the adjusted dependent control setting level to control the device; displaying the adjusted independent control setting level and the at least one adjusted dependent control setting level, and implementing both the adjusted independent control setting level and the at least one adjusted dependent control setting dependent to control the device by actuating a batch setting acceptance operation.

BRIEF DESCRIPTION OF THE DRAWINGS

A preferred embodiment and best mode of the invention is illustrated in the attached drawings that are described as follows.

DESCRIPTION OF AN EMBODIMENT OF THE INVENTION

Figure 1:
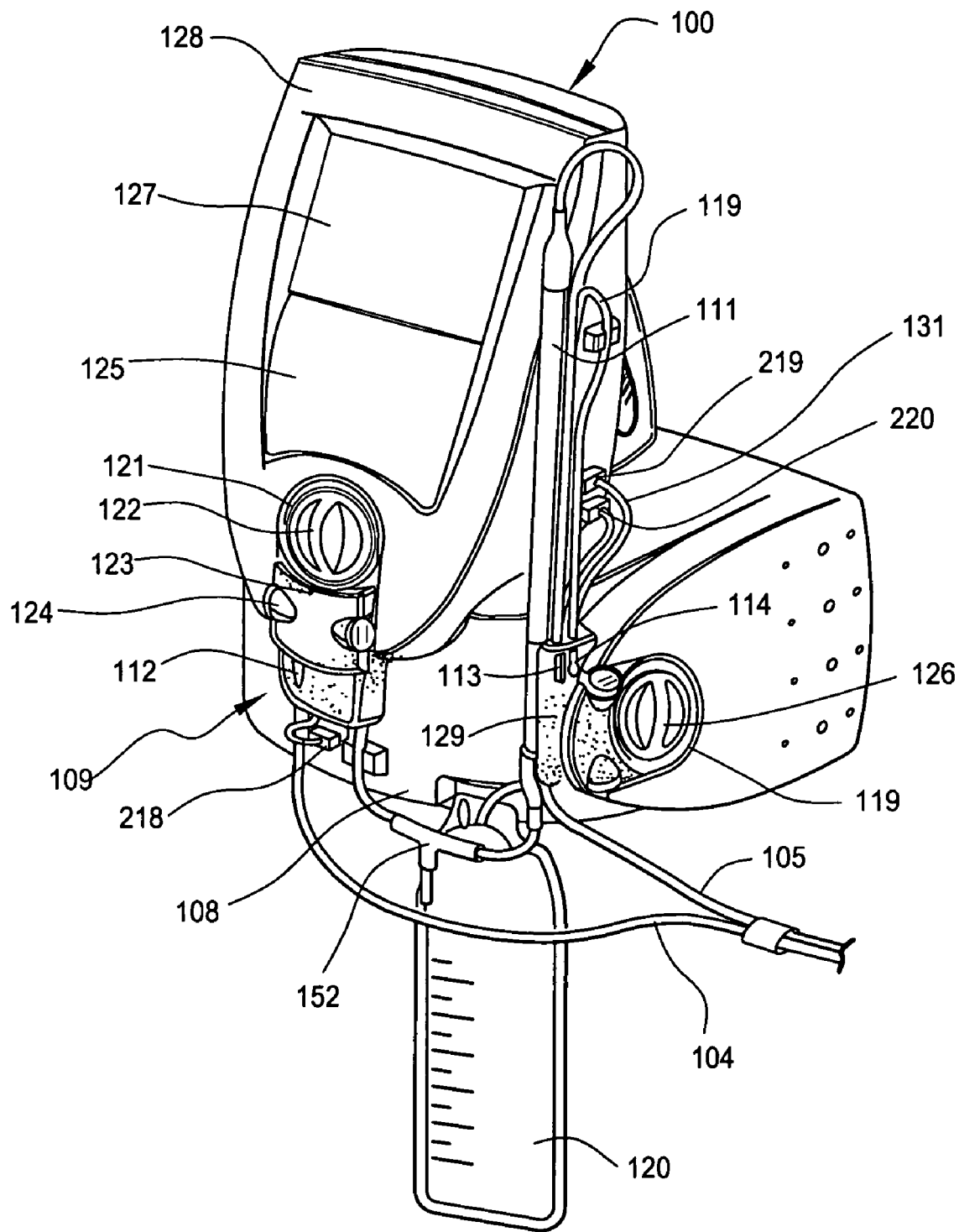
FIG. 1 is a perspective view of an intravenous blood ultrafiltration system using a disposable blood circuit and a user interface.

FIG. 1 shows an intravenous blood ultrafiltration system 100 for treating a patient (not shown) suffering from fluid overload. The console 128 has a front panel with a membrane keypad 125 and a graphics display 127. A Graphical User Interface (GUI) using the keypad and display is used with a single use disposable extracorporeal circuit for ultrafiltration (the ultrafiltration set) of blood to treat fluid overload in patients in a hospital setting. To remove excess fluid from the patient the ultrafiltration set 109 is mountable on the console 128 that is equipped with two pumps. The blood pump 122 moves and controls the flow rate of blood through the tubing and filter of the ultrafiltration set. The filtrate pump 126 moves and controls the flow rate of ultrafiltrate. The ultrafiltration set contains a disposable blood/ultrafiltrate fluids circuit 108 with an integral blood separation filter 111 and integrated pressure sensors 112, 113. When the set is assembled on the system pump console and is connected to the patient, the set forms fluids paths for blood and ultrafiltrate. The system pump console interfaces with the fluid path via sensors and pumps. The Graphical User Interface (GUI) is an integral part of the system console. The GUI gives operator information about treatment, and assists in identifying faults in the fluid path, and causes of alarms.

Figure 2:
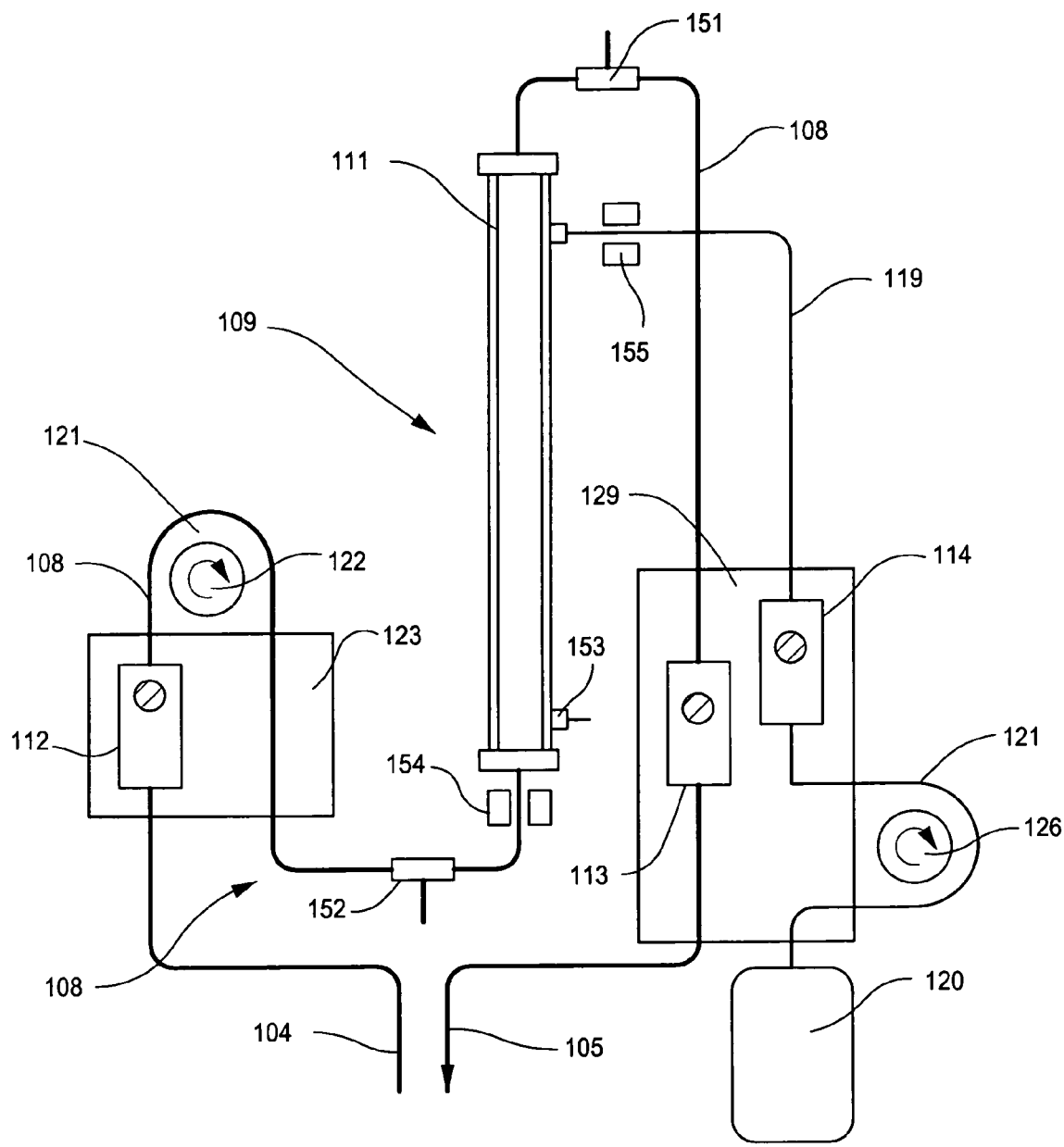
FIG. 2 is a schematic diagram showing a fluid path of blood and removed fluids for the blood circuit used with the ultrafiltration system shown in FIG. 1.

To initiate ultrafiltration treatment, two plastic intravenous cannulae or needles are introduced into suitable peripheral veins of the patient for the withdrawal and return of the blood. The needles are attached to withdrawal tubing 104 and return tubing 105, and secured to skin with attachments, such as adhesive strips. The withdrawal and return tubing, 104 and 105, form portions of a continuous blood fluid passage 108 that extends through a disposable blood circuit 109 (FIG. 2). The disposable blood circuit cartridge 109 is attached to the console 128 to perform ultrafiltration treatment.

Tubing sections of the blood circuit extend through cartridge 109 and form additional conduit links in the blood fluid passage 108. These tubing links are coupled to a blood filter 111 and blood pressure sensors 112, 113, that are contiguous with the tubing and form sections of the blood fluid passage 108. In other embodiments, the blood filter 111 may be supplied separately from other components of the blood circuit. The filter is connected to the blood circuit cartridge by the operator before treatment.

The disposable blood ultrafiltration circuit cartridge may be supplied separate from the system, and packaged in a sterile package. The circuit is generally intended to be used for one single RRT treatment and is not reused. The cartridge is inserted into the console 128 by threading the tubing loops 121 in the blood passage 108 and ultrafiltrate discharge tubing 119 over the rims of roller pumps 122 and 126, respectively. As pumps 122 and 126 rotate, they slidably engage the tubing and force blood and ultrafiltrate fluids to move through the cartridge fluid passages.

Figure 9:
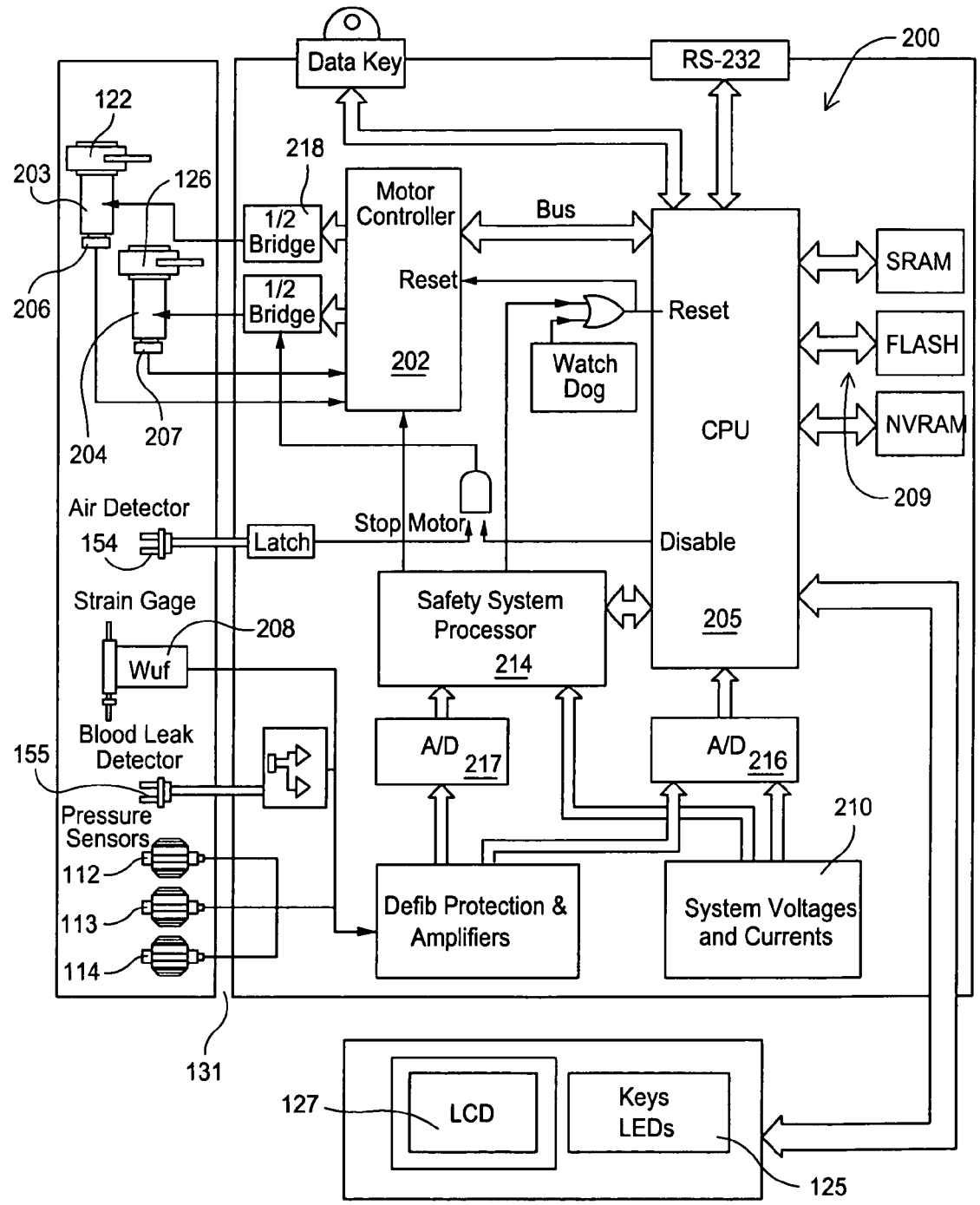
FIG. 9 illustrates the electrical architecture of the ultrafiltration controller system.

Microprocessor pump drivers control the rotational speed of the pump and the flow rate of the blood and ultrafiltrate through the fluid paths of the extracorporeal circuit. The pump drivers are part of the console 128 and are controlled by a microprocessor controller 205 within the pump console (FIG. 9).

The tubing of the blood circuit cartridge 109 may be mounted in molded-plastic housing cartridges 123 that fit into recesses in the surface of the console 128 and snaps into the console with latches 124. A blood withdrawal pressure sensor 112 is mounted to an inside surface of one of the cartridge housings 123. A pressure sensor 113 for the blood return tube 105 and an ultrafiltrate pressure sensor 114 are mounted to an inside surface of the second cartridge housing 129. Blood pressure sensors 112 and 113 and ultrafiltrate pressure sensor 114 include transducers that convert pressures into electrical signals carried by signal wires 131 that are connected to a controller 200 (FIG. 9) via the plug-in connectors on the console 128. Filter 111 may be a hemofilter having a polysulfone hollow fiber membrane.

The console 128 has a front display 127, keypad 125 and first roller pump 122. The console 128 also has a side, orthogonal to the front, which has the second roller pump 126. The blood circuit cartridges 109 are mounted on the console 128 by folding the blood circuit cartridge around the front and side of the console. The tubing for the bloodline in the cartridge is inserted on the front roller pump 122. The filter 111 and tubing for the side roller pump 126 is attached to and mounted on the side of the console. By using both the front and side of the console to mount the blood cartridge, the front area of the console is substantially reduced. In particular, by folding the blood circuit around the front and side of the console, the area needed on the front face of the console to support the blood circuit is effectively reduced by one-half. Thus, the console can have a smaller front side and have a more compact and appealing appearance.

FIG. 2 is a schematic diagram of the blood and filtrate flow through the ultrafiltration system 100 known as a system flow path. The system symbolically depicted in the FIG. 2 is designed primarily to perform SCUF (Slow Continuous Ultrafiltration) but can be converted for other RRT treatment modalities. The lower port 153 of the hemofilter 111 is plugged for SCUF. If dialysis is desired, a source of dialysate fluid can be connected to this port 153 and the port opened to receive the fluid into the filter. Dialysis fluid will circulate through the filter casing and interface with blood through the hollow fiber membrane so that clearance can be obtained via the diffusion of solute. For a dialysis mode, dialysate may circulate through the filter in a direction opposite to blood by reversing the filtrate pump 126. Alternatively the access port 152 in the circuit tubing 108 can be used to infuse the replacement solution. Ultrafiltration rate can be increased proportionally by speeding up the pump 122 so that clearance can be obtained by convective transport of solute with ultrafiltrate. Similarly, the post-filter port 151 can be used to infuse the replacement solution if desired.

Regardless of the RRT modality desired, the basic principles of the apparatus design remain the same. Blood that is withdrawn from the patient flows into the withdrawal tubing 104 and enters the blood passage 108 of the blood circuit. Blood passes through and is treated in the hollow fibers of the filter 111, and is returned to the patient via the return tube 105. Ultrafiltrate, effluent or dialysis solution passes through the filter casing surrounding the blood filled hollow fibers. Blood pump 122 generates and controls the flow of blood. Filtrate pump 126 generates and controls the flow of ultrafiltrate. Pump segment tubing loops 121 are attached to cartridges 123 and 129 to assist loading of pumps and prevent tubes from kinking. The ultrafiltrate line pressure sensor 114 is integrated into the same cartridge as the blood return sensor 113. Pressure sensors 112, 113 are integral to the blood passage 108 in the cartridges 123 and 129. These sensors are disposed in blood passage 108, such that a diaphragm of the sensor, which is the device that is in fluid contact with the load and directly responds to the blood pressure, is adjacent the blood passage.

From the blood pump 122 to the filter 111, blood traverses through an air detector sensor 154. The air detector sensor may use attenuation of ultrasonic sound waves in fluid to detect air bubbles in the blood passage 108. An air bubble indicates a leak or break in the blood circuit. An air bubble can be dangerous if passed into the bloodstream of the patient. Accordingly, the detection of an air bubble will cause an alarm and stop the pumps.

Similar to the blood pressure sensors in the blood passage of the circuit, the pressure sensor 114 (which may include a diaphragm in fluid contact with the filtered fluid) for the ultrafiltrate is integrally formed in the filtrate tubing 119 of the circuit between the filter 111 and the ultrafiltration bag 120. Ultrafiltrate exiting the filter 111 passes through a blood leak detector 155. The blood leak detector is a photometric device that uses infrared light beam to detect presence of red blood cells in the ultrafiltrate. The detection of blood in the ultrafiltrate line indicates a filter failure because blood cells should not normally pass through the filter membrane into the filtrate line.

The blood and ultrafiltrate pressure sensors 112, 113 and 114 are included in the disposable cartridge and are intended for one-time use. Air detector 154 and blood leak detector 155 are mounted on the system console and have means to clamp around the plastic tubing that forms the fluid passage. Infrared and ultrasonic waves can penetrate the plastic tubing wall. The sensors each have a generally straight and hollow fluid passage that is coupled to the blood or filtrate tubing in the cartridge. The passages in the sensors are contiguous with the blood and ultrafiltrate passage of the cartridge.

Electrical signals are transmitted by the sensors to the pump system 200 (FIG. 9) through electrical signal lines, e.g., wires. A microprocessor controller in system 200 receives the pressure signals via the wire lines and determines the pressure level of the blood or ultrafiltrate in the fluid passage in which the associated sensor is positioned. Similarly the system receives information of presence of air in the blood flow or blood in ultrafiltrate.

Figure 3:
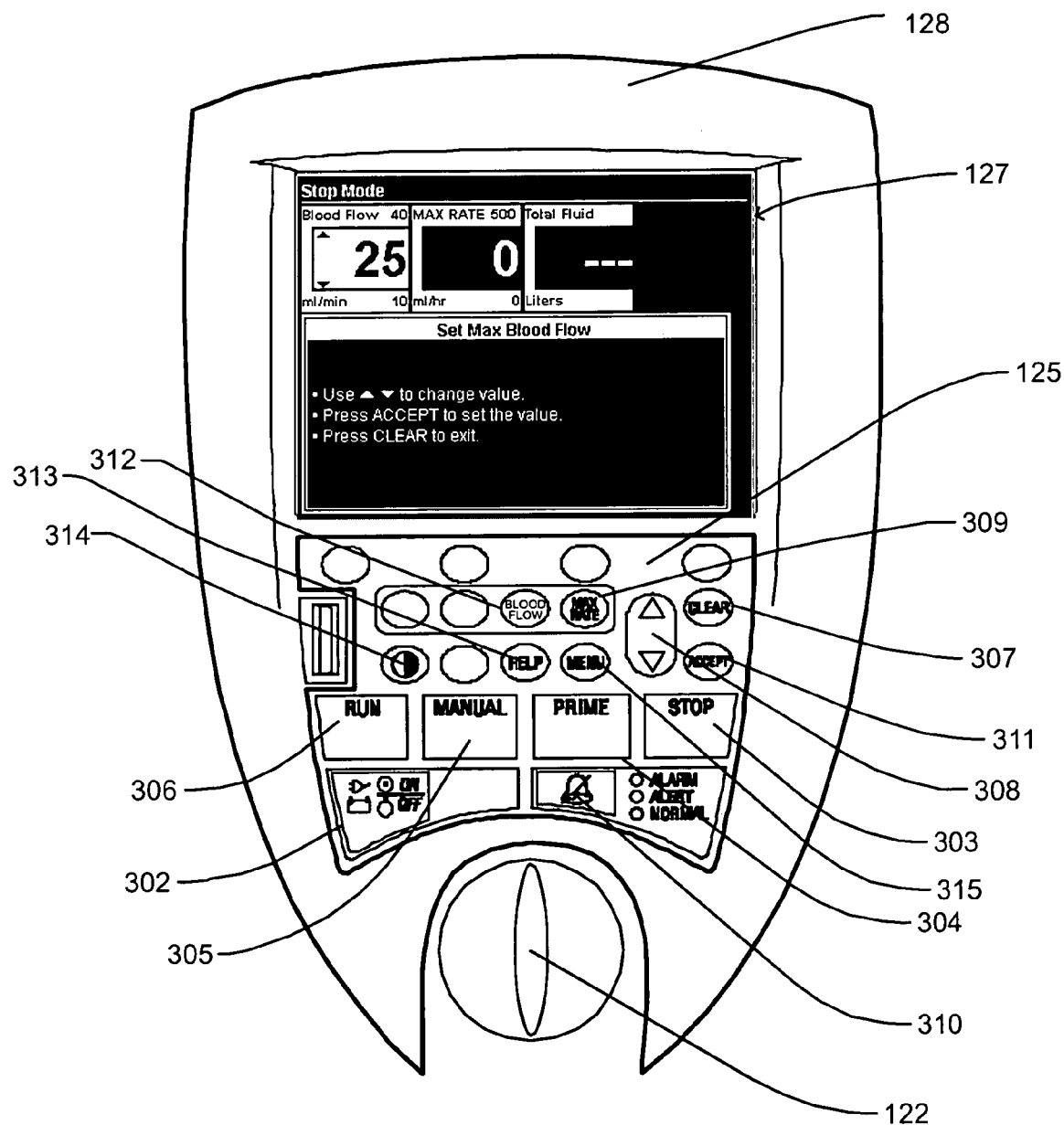
FIG. 3 is an enlarged view of the user interface area of the device shown in FIG. 1 with a graphics screen.

FIG. 3 illustrates one embodiment of the User Interface for the Ultrafiltration system 100 and, in particular, the console 128. The membrane control panel 125 includes 15 operational keys and 7 non-operational keys available for future use. The key membrane panel also displays information to the user regarding, for example:

The mode of operation (e.g., STOP, MANUAL, PRIME or RUN) is indicated by the status light emitting diodes (LEDs) on the top left-hand corners of the corresponding key 303, 304, 305 and 306.

The status of the system, ALARM, ALERT or NORMAL is indicated by corresponding the corresponding status LEDs.

Whether ALARM SILENCE is active or not is indicated by the alarm silence LED and key 310.

The source of power, e.g. battery or wall socket, is indicated by the LED next to the battery and AC plug symbols.

Whether the device is powered ON or OFF by an LED next to the ON/OFF key 302.

The ON/OFF key 302 is used to power on the system. The key is in the ON position when one of the mode keys has an LED (light emitting diodes) are illuminated. A momentary press turns power ON. The key 302 is depressed for one second before the device is powered OFF. When the green LED beside the plug symbol is lit it indicates that AC is the source of power. When the green LED beside the battery symbol is lit it indicates that battery is the source of power.

The STOP key 303 may be used to stop the system and is available in all modes. When the STOP key is activated, it immediately stops the rotation of the blood and ultrafiltrate pumps and thereby ceases the flow of blood and filtrate through the blood circuit. Upon power on, the STOP mode is the default mode.

The PRIME mode is activated by key 304 and primes the circuit with saline to remove air from the circuit before connecting the catheters to the patient. In the PRIME mode, the system pumps saline for 3 minutes, and then must detect no air in the circuit for 40 seconds (while the saline flows) consecutively before PRIME is deemed successful.

The MANUAL mode is activated by key 305 and replaces the saline in the circuit with blood from the patient or is used to advance an air bubble. The MANUAL mode begins immediately from STOP mode when the MANUAL key is pressed. To operate the system in MANUAL mode, the user continually presses the MANUAL key. When the MANUAL key 305 is released or a one-minute manual time-out period expires, the system will automatically enter the STOP Mode. The MANUAL key may only be accessed while the console is in the STOP mode and only if the PRIME mode has successfully completed. If the current mode is RUN mode, pressing the MANUAL key has no effect.

The RUN Mode is activated by key 306 and withdraws and infuses blood continually and simultaneously from and to the patient while performing ultrafiltration at the set MAX RATE. Ultrafiltration is performed when the blood flow through the circuit 109 exceeds 40 ml/min or some other minimal flow setting. The RUN key may be accessed from the STOP mode after the PRIME mode has successfully completed. The ACCEPT key 311 confirms that the user intends to enter the PRIME mode or a particular MENU Function.

The CLEAR key 307 clears active alarms, clears the ALARM SILENCE function, clears an active request before it has been accepted and exits from menu sub-functions. If the alarm condition is still present, the alarm will re-annunciate after the CLEAR key has been pressed. If the PRIME key is pressed in error in STOP mode (active request), the CLEAR key can be used to clear the request and return the system to STOP mode. The UP and DOWN arrows 308 allow the user to scroll through the menu options, scroll help text, and increase and decrease user settings such as MAX RATE, Alarm Volume and Contrast.

The UP ARROW and DOWN ARROW keys 308 allow the user to select menu options, scroll the display, set flow rates, set date and time, etc. These keys automatically repeat if held down. The MAX RATE key 309 allows the user to set a maximum ultrafiltrate rate. The controller 200 (FIG. 9) may automatically reduce the filtrate rate during reduced blood flow, if the blood hemocrit value exceeds a predetermined value, if the filtrate bag becomes too heavy or if some other predetermined condition arises and is detected by the controller. The ALARM MUTE key 310 allows the user to silence the audible portion of the current alarm/alert for up to 2 minutes. Any new alarms/alerts will cancel this function, as will pressing the CLEAR key 307.

The ACCEPT key 311 is used to confirm user settings such as flow rates, date and time, speaker volume, etc. The ACCEPT keys allows the settings to be entered as a batch of settings. The BLOOD FLOW key 312 allows the user to set the maximum blood flow rate. The controller 200 (FIG. 9) may automatically reduce blood flow through the circuit if an occlusion is detected in the blood flow, and if the negative withdrawal pressure or if the positive infusion pressure become excessive. The HELP key 313 causes the display of information about the current state of the system. If pressed, the HELP key will display the function of the current mode when no alarms are present. The CONTRAST key 314 allows the user to adjust the contrast of the LCD display 127 (FIG. 1).

When pressed, the MENU key 315 causes the display to show the following options: Alarm/Event History, Change Date and Time, Change Speaker Volume, Disable Blood Leak Detector, About S-100, Loading the UF 500 Set. The MENU options are available from the modes STOP, PRIME and RUN. When selected, the menu option allows the operator to select various operational modes including: The Alarm/Event History display mode shows the last 200 active alarms/events along with the time and date of occurrence. The Change Date and Time mode prompts the user to change the date and time. The Change Alarm Volume mode allows the user to adjust the main alarm volume between 65 dBA and 80 dBA. The Disable Blood Leak Detector mode allows the user to disable or enable the blood leak detector. The about S-100 is an informational display mode which shows the user to see which hardware and software revisions the system 100 is running, as well as hours of system operation. The loading the UF 500 Set display mode provides an interactive step-by-step procedure for loading the blood circuit 109 (FIG. 2) onto the console 128 (FIG. 1).

Figure 4:
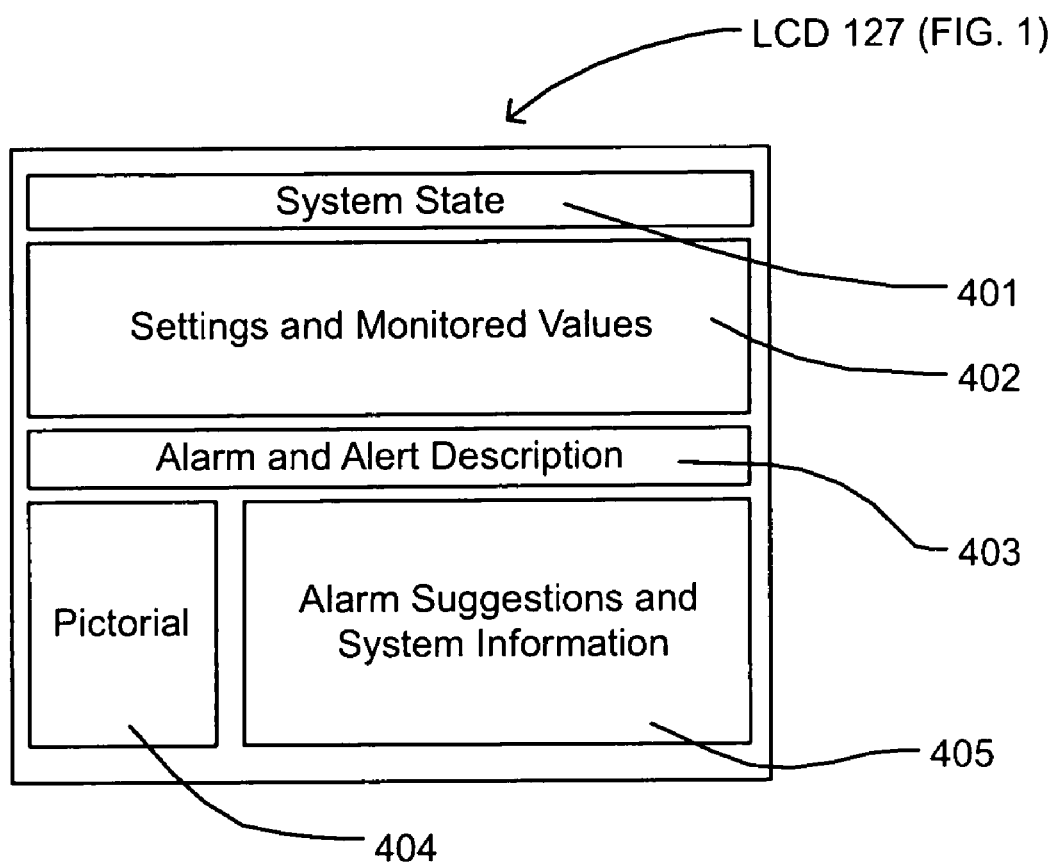
FIG. 4 is a schematic diagram of the LCD screen layout.

FIG. 4 illustrates the information displayed on the LCD 127 of the pump console. The Liquid Crystal Display (LCD) 127 (FIG. 1) may be a monochrome or color flat panel display. The LCD screen has a large viewing area, and improves the user friendliness of the console 128 by providing helpful data to the user on how to solve each alarm condition. The LCD screen 127 is divided into five areas: (i) the system state area 401 shows the current system mode and length of time for that mode, (ii) the Settings and Monitored Values area 402 shows the user set MAX RATE and BLOOD FLOW in a manner that allows for comparison of these two flow rates, (iii) the Alarm and Alert Description area 403 displays the text of the active alarm, (iv) the Pictogram area 404 shows the affected system element, e.g., section of the blood circuit, to the user by flashing that affected section to draw the user's attention to the source of the alarm, and (v) the Alarm Suggestion and system Information area 405 displays suggested fixes for alarms. The LCD display is also used to display help and to navigate the user through the menu options.

FIGS. 5 through 8 are examples of screens which may appear during the setting of BLOOD FLOW and MAX RATE of filtration. An exemplary method for setting BLOOD FLOW and MAX RATE is described below. The BLOOD FLOW and MAX RATE are batch adjustable. Both the BLOOD FLOW and MAX RATE may be adjusted as proposed changes before a setting change is implemented by the ACCEPT keys, so as to allow the user to switch between settings before implementing the proposed setting change by pressing the ACCEPT key 311 (FIG. 3). The console automatically adjusts the MAX RATE or BLOOD FLOW to maintain the MAX RATE (filtrate) at no more than some threshold level, e.g., 21%, of the BLOOD FLOW. If the user lowers the BLOOD FLOW such that this ratio is exceeded, the console automatically lowers the MAX RATE to maintain the blood to filtrate ratio at or below 21%. If the user raises the MAX RATE, the console will automatically raise the BLOOD FLOW to maintain the ratio at or below 21%.

Figure 5:
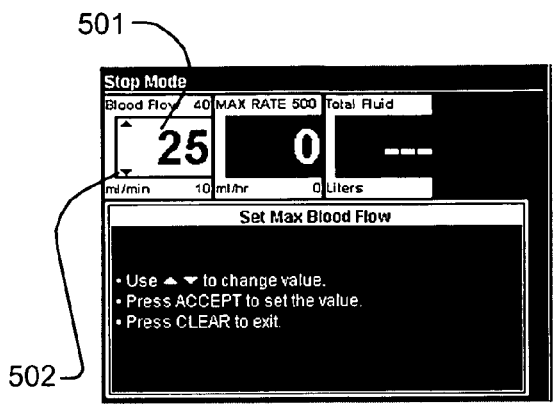
FIGS. 5 through 8 are examples of screens which may appear during the setting of BLOOD FLOW and MAX RATE.

To set the BLOOD FLOW, the user first presses the BLOOD FLOW key 312 (FIG. 3), resulting in the display shown in FIG. 5. The setting being changed is highlighted in reverse-video 501, and arrow symbols which match the arrow keys 308 (FIG. 3) are drawn in reverse video to the left of the parameter which is being adjusted 502. The user has a visual reference regarding which setting is being altered. The user adjusts the BLOOD FLOW by pressing the UP ARROW and DOWN ARROW keys 308 (FIG. 3), which increase or decrease (respectively) the proposed setting by 5 ml/min per key press. The limits for the BLOOD FLOW setting are, for example, 0 to 40 ml/min, inclusive. If the user attempts to select a value beyond this range (using the arrow keys), the console will ignore the request and emit a chirp sound to indicate an invalid key press. When the user has reached the desired BLOOD FLOW and/or MAX RATE proposed values, the user must press the ACCEPT key 311 (FIG. 3) to implement the proposed settings.

The user may at any time press the MAX RATE key 309 (FIG. 3) to adjust the proposed MAX RATE setting as described below without changing or committing to the proposed BLOOD FLOW. The user may then resume changing the proposed BLOOD FLOW setting by pressing the BLOOD FLOW key 312 (FIG. 3) without changing or committing to the proposed MAX RATE. The user may alternate between these settings as often as desired.

Figure 6:
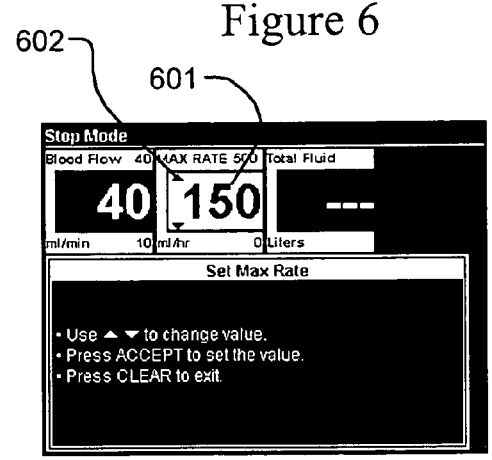

To set the MAX RATE of filtration, the user first presses the MAX RATE key 308 (FIG. 3), resulting in the display shown in FIG. 6. The setting being changed is highlighted in reverse-video in section 601, and arrow symbols 602 which match the arrow keys 308 (FIG. 3) are drawn in reverse video to the left of the parameter which is being adjusted. The user has a visual reference regarding which setting is being altered. The user adjusts the MAX RATE by pressing the UP ARROW and DOWN ARROW keys 308 (FIG. 3), which increase or decrease (respectively) the proposed setting by 10 ml/hr per key press. The limits for the MAX RATE setting are, for example, 0 to 500 ml/hr, inclusive. If the user attempts to select a value beyond this range (using the arrow keys), the console will ignore the request and emit a chirp sound to indicate an invalid key press. When the user has reached the desired BLOOD FLOW and/or MAX RATE proposed values, the user must press the ACCEPT key 311 (FIG. 3) to activate the proposed settings.

No changes to the actual BLOOD FLOW or MAX RATE are actually implemented by the console 128, until the ACCEPT key 311 (FIG. 3) is pressed. Pressing no key for 10-30 seconds or pressing any other key other than UP/DOWN ARROW key 308 (FIG. 3), MAX RATE key 309 or BLOOD FLOW key 312 will result in the cancellation of the BLOOD FLOW and the MAX RATE changes, and the original BLOOD FLOW and MAX RATE settings will remain unchanged.

Figure 7:
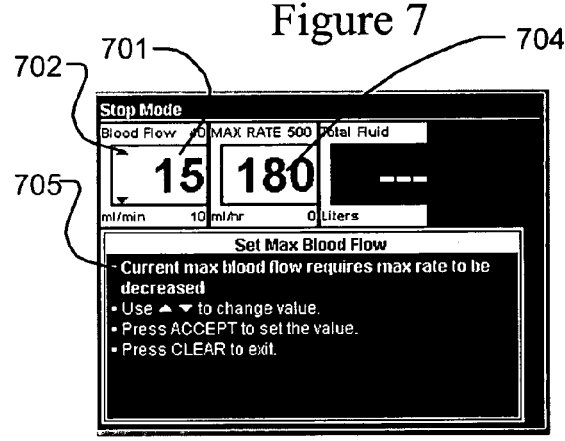

If the user attempts to set a BLOOD FLOW which is too low to maintain the current MAX RATE at less than or equal to (<=) 21% of BLOOD FLOW, software automatically reduces the proposed MAX RATE, emits a beep tone, highlights the change in reverse-video 704, and adds a message to the display 705, as shown in FIG. 7. The arrows remain displayed to the left of the rate which is being adjusted 701. If the user presses the ACCEPT key 311 (FIG. 3) with both proposed settings highlighted as shown in FIG. 7, both changes will immediately take effect. If the user increases the BLOOD FLOW setting (by pressing the UP ARROW key 308 [FIG. 3]) back to a setting which is high enough to maintain the original (or proposed) MAX RATE, the original value is re-displayed unhighlighted and the added text is removed, as shown in FIG. 5.

The displayed MAX RATE may be automatically adjusted multiple times depending on the original MAX RATE settings. As shown in FIG. 7, as the user presses the DOWN ARROW key 308 (FIG. 3) the proposed BLOOD FLOW setting will reduce to 10 ml/min and the console automatically reduces the proposed MAX RATE to 120 ml/hr. Table 1 shows the highest MAX RATE allowed for each BLOOD FLOW setting.

TABLE 1

| BLOOD FLOW Setting | Highest MAX RATE Allowed |
|---|---|
| 10 | 120 |
| 15 | 180 |
| 20 | 250 |
| 25 | 310 |
| 30 | 370 |
| 35 | 440 |
| 40 | 500 |

Figure 8:
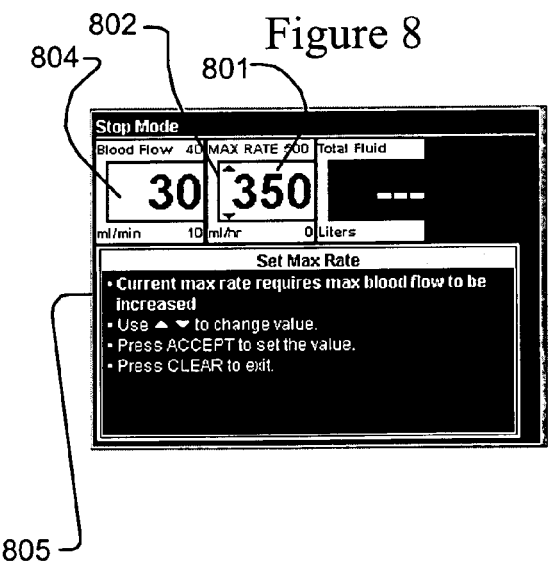

Similarly, when the user attempts to set a MAX RATE of filtration which is too high to maintain the current BLOOD FLOW at greater than or equal to (<=) 21% of MAX RATE, the console software automatically raises the BLOOD FLOW, emits a beep tone, highlights the proposed change in reverse-video 804, and adds a message 805 to the display, as shown in FIG. 8. The arrows remain displayed to the left of the rate which is being adjusted 802. If the user presses the ACCEPT key 311 (FIG. 3) with both settings highlighted as shown in FIG. 8, both changes will then immediately take effect. If the user decreases the MAX RATE setting (by pressing the DOWN ARROW key 308 (FIG. 3) back to a setting which is low enough to maintain the original (or proposed) BLOOD FLOW, the original value is re-displayed unhighlighted and the added text 805 is removed, as shown in FIG. 6.

The displayed BLOOD FLOW may be automatically adjusted multiple times depending on the original BLOOD FLOW setting. As shown in FIG. 8, when the user presses the UP ARROW key 308 (FIG. 3) several times the proposed MAX RATE setting will increase to 380 ml/hr, at which point the console will automatically raise the proposed BLOOD FLOW to 35 ml/hr. Table 1 shows the highest MAX RATE allowed for each BLOOD FLOW setting.

As is apparent from the above discussion regarding the setting of the parameters for MAX RATE of filtration and of BLOOD FLOW, the parameter that is being manually selected by the operator is treated as an independent parameter and the other parameter depends on the independent parameter in that the other parameter is automatically adjusted depending on the setting of the independent parameter. For example, when the operator is selecting a level for BLOOD FLOW the console software automatically adjusts the proposed MAX RATE so as to limit the filtration to no more than some predetermined proportion, e.g., 21%, of the selected BLOOD FLOW. The adjustment is made to the proposed MAX RATE and is based on the selected BLOOD FLOW, both of which have not yet been implemented to control the flow of blood and filtrate through the circuit. The console LCD will display the proposed BLOOD FLOW and MAX RATE so that the operator may decide whether to implement the displayed rates by depressing the ACCEPT key.

If the operator wishes to change the MAX RATE that was automatically determined based on the selection of the BLOOD FLOW, the operator may press the MAX RATE key to manually select a maximum filtration rate. By selecting the MAX RATE key, the filtration limit become the independent parameter and the BLOOD FLOW becomes the dependent parameter that is automatically adjusted based on the selected MAX RATE filtration limit. For example, if the MAX RATE is manually increased, the console software will increase the proposed blood flow rate to ensure that the filtration limit does not exceed a predetermined proportion of the blood flow through the circuit. As with the selection of the BLOOD FLOW, the selection of the MAX RATE and the automatic adjustment to BLOOD FLOW are not implemented until accepted by the operator. Accordingly, the BLOOD FLOW may be an independent parameter when the operator is manually selecting the blood flow rate and may be a dependent parameter when the operator is selecting a limit for the filtration rate. Similarly, the MAX RATE of filtration may be an independent or dependent parameter depending on whether the operator is manually selecting the blood flow rate or the filtration rate limit.

As is evident from the above discussion regarding the relationship between blood flow and maximum filtrate rate, the settings in an RRT type device may be mathematically related to each other such that changing one setting will have an effect on another. The user interface disclosed herein enables the user to adjust any of the possible settings in any sequence while enacting the functional limitation of the setting being changed upon all other related settings (without immediately actually changing the operation of the device).

The term independent control setting pertains to the current setting being manually adjusted by the user and the term dependent control setting pertains to all related settings which are affected by the change of the independent control setting. Consider, for example, a device had manually adjustable settings both flow rate and time. These settings each related to the other and together are related to a defined preset volume. In this example, time equals volume/flow rate and flow rate equals volume/time. When the flow rate is manually adjusted it is treated as the independent control setting, and the time setting is automatically recalculated to show the time it would take to fill the preset volume and vice versa. Conversely, if time is manually adjusted it becomes the independent control setting, and the flow rate (as the dependent setting) would be automatically adjusted to ensure that the preset volume was filled in the desired time. Accordingly, the setting which is being manually adjusted is treated as the independent control setting and the setting which is being automatically modified by the relationship rule between time, flow rate and preset volume is the dependent control setting.

FIG. 9 illustrates the electrical architecture of the ultrafiltration controller system 200 (Part of 100 in FIG. 1), showing the various signal inputs and actuator outputs to the controller. The user-operator inputs the desired ultrafiltrate extraction rate into the controller by pressing buttons on a membrane interface keypad 125 (FIG. 1) on the controller. Other user settings may include the maximum flow rate of blood through the system, maximum time for running the circuit to filter the blood and the maximum ultrafiltrate rate. The settings input by the user are stored in a memory and read and displayed by the controller CPU 205 (central processing unit, e.g., microprocessor or micro-controller) on the LCD screen 127 (FIG. 1). The CPU 205 is equipped with a memory system 209 where software code and data are stored. A data key unique to the blood circuit 109 is inserted in the console 128 to enable pump operation and to capture operational data of the system.

The controller CPU 205 regulates the pump speeds by commanding a motor controller 202 to set the rotational speed of the blood pump 122 (FIG. 1) to a certain speed specified by the controller CPU. Similarly, the motor controller 202 adjusts the speed of the ultrafiltrate pump 126 (FIG. 1) in response to commands from the controller CPU and to provide a particular filtrate flow velocity specified by the controller CPU.

Feedback signals from the withdrawal pressure sensor 112 (FIG. 1), ultrafiltrate pressure sensor 114 and blood return pressure sensor 113 are converted from analog voltage levels to digital signals in an A/D converter 216, 217. The digital pressure signals are provided to the controller CPU as feedback signals and compared to the intended pressure levels determined by the CPU. This allows the CPU 205 software to detect disconnections and occlusions in the fluid path. In addition, the digital pressure signals may be read by the Safety System Processor 214. This ensures redundancy of critical safety monitoring functions of the system.

The motor controller 202 controls the velocity, rotational speed of the blood and filtrate pump motors 203, 204. Rotational encoders 206 and 207 mounted to the rotational shaft of each of the motors as feedback provide quadrature signals (e.g., a pair of identical cyclical digital signals, but 90° out-of-phase with one another). These signal pairs are fed to a quadrature counter within the motor controller 202 to give both direction and position. The direction is determined by the signal lead of the quadrature signals. The position of the motor is determined by the accumulation of pulse edges. Actual motor velocity is computed by the motor controller as the rate of change of position. The controller calculates a position trajectory that dictates where the motor must be at a given time and the difference between the actual position and the desired position is used as feedback for the motor controller. The motor controller then modulates the percentage of the on time of the pulse width modulation (PWM) signal sent to the one-half 218 bridge circuit to minimize the error. A separate quadrature counter is independently read by the Controller CPU 205 to ensure that the Motor Controller 202 is correctly controlling the velocity of the motor. This is achieved by differentiating the change in position of the motor over time. Additional source of information about the performance of the fluid path of the system are the digitized system voltages and currents 210. The CPU 205 can determine such events as a jammed pump 122 or 126 or an occluded filter 111 by continuously monitoring feedback from encoders 206 and 207 and current consumed by DC motors 203 and 204.

The CPU 205 monitors each of the critical signals, including signal indicative of blood leaks 155, pressures in blood circuit 112, 113 114, weight (Wuf) 208 of the filtrate bag, motor currents, air in bloodline detector 154 and motor speed/position. The CPU has stored in its memory safety and alarm levels for various operating conditions of the ultrafiltrate system. By comparing these allowable preset levels to the real-time operating signals, the Safety System Processor 214 can determine whether a safety alarm should be issued, and has the ability to independently stop both motors and reset the motor controller 202 and controller CPU 205 if necessary. It can also pinpoint the location of the alarm source along the fluid path of the machine.

Although the present invention has been described in terms of a particular embodiment, it is not intended that the invention be limited to that embodiment. Modifications of the disclosed embodiment within the spirit of the invention will be apparent to those skilled in the art. The scope of the present invention is defined by the claims that follow.

What is claimed is:

1. A method for batch implementation of settings in a renal replacement therapy device comprising at least one fluid pump connectable to a detachable extracorporeal blood circuit, at least one pressure sensor monitoring pressure in a blood line of the blood circuit, a controller regulating the at least one fluid pump according to stored control settings and inputs for the at least one pressure sensor and a user interface, said method comprising:
   a. displaying on the user interface a plurality of control settings which may be manually selected by an operator;
   b. selecting a first independent control setting of the plurality of control settings;
   c. adjusting the first independent control setting to a first independent control setting level selected by an operator;
   d. temporarily storing the first independent control setting level, without implementing the first independent control setting level to control the device;
   e. automatically establishing a limit for a first dependent control setting level based upon the first independent control level, without first implementing the first independent or first dependent control setting level to control the device;
   f. after step e, implementing both the second independent control setting level and the second dependent control setting level to control the device during a first renal replacement therapy by actuating a batch setting acceptance operation;

g. selecting the first dependent control level for manual adjustment, wherein the selection converts the first dependent control setting to a second independent control setting and converts the first independent control setting to a second dependent control setting;

h. adjusting the second independent control setting to a second independent control setting level selected by an operator;

i. temporarily storing the second independent control setting level, without implementing the second independent control setting level to control the device;

j. automatically establishing a limit for the second dependent control setting level based upon the first independent control level, without first implementing the second independent control setting level or the second dependent control setting levels to control the device, and k. after step j, implementing both the second independent control setting level and the second dependent control setting level to control the device during a second renal replacement therapy by actuating a batch setting acceptance operation.

2. A method for batch implementation of settings as in claim 1 further comprising issuing an alarm if the operator selects a level of the first or second control setting level that exceeds an established limit for the corresponding dependent control setting.

3. A method for batch implementation of settings as in claim 1 further comprising clearing the first independent control setting level and the first dependent control setting level at or before the actuation of the batch setting acceptance operation.

4. The method for batch implementation of settings as in claim 1 wherein the actuating of the batch setting acceptance is performed by an operator actuating an acceptance input of the user interface.

5. The method for batch implementation of settings as in claim 1 wherein the actuating of the batch setting acceptance is performed by an operator depressing an acceptance input key on the user interface.

6. The method for batch implementation of settings as in claim 1 wherein selecting the first and second independent control settings further comprises highlighting the independent control setting on the display.

7. The method for batch implementation of settings as in claim 1 wherein selecting the first and second independent control setting further comprises adjusting the independent control setting by increasing or decreasing a value of the setting through an input on the user interface.

8. The method for batch implementation of settings as in claim 1 wherein the first independent control setting is a blood limit of blood flowing through the circuit and the first dependent control setting is a filtrate limit of filtrate flowing from a blood filter in the circuit.

9. The method for batch implementation of settings as in claim 1 wherein the renal replacement therapy device is an ultrafiltration device.

10. The method for batch implementation of settings as in claim 1 wherein step (e) further comprises automatically establishing a limit for each of a plurality of first dependent control setting levels based upon the first independent control level, without first implementing the first independent or any of the first dependent control setting levels to control the device, and wherein in step (g) the selected first dependent control level is selected from the plurality of first dependent control setting levels.

11. The method for batch implementation of settings as in claim 10 wherein said first dependent control setting levels other than the second independent control setting become second dependent control settings.

12. A method for batch implementation of settings in a renal replacement therapy device comprising at least one fluid pump connectable to a detachable extracorporeal blood circuit at least one pressure sensor monitoring pressure in a blood line of the blood circuit, a controller regulating the at least one fluid pump according to stored control settings and inputs for the at least one pressure sensor and a user interface, said method comprising:

a. displaying on the user interface a plurality of control settings which may be manually selected by an operator:

b. selecting a first independent control setting of the plurality of control settings;

c. adjusting the first independent control setting to a first independent control setting level selected by an operator;

d. temporarily storing the first independent control setting level, without implementing the first independent control setting level to control the device;

e. automatically establishing a limit for a first dependent control setting level based upon the first independent control level, without first implementing the first independent or first dependent control setting level to control the device, wherein the first independent control setting is a blood pressure limit of blood flowing through the circuit and the first dependent control setting is a filtrate pressure limit of filtrate flowing from a blood filter in the circuit;

f. selecting the first dependent control level for manual adjustment, wherein the selection converts the first dependent control setting to a second independent control setting and converts the first independent control setting to a second dependent control setting;

g. adjusting the second independent control setting to an second independent control setting level selected by an operator;

h. temporarily storing the second independent control setting level, without implementing the second independent control setting level to control the device;

i. automatically establishing a limit for the second dependent control setting level based upon the first independent control level, without first implementing the second independent control setting level or the second dependent control setting levels to control the device, and j. implementing both the second independent control setting level and the second independent control setting level to control the device by actuating a batch setting acceptance operation.

13. A method for batch implementation of settings in a renal replacement therapy device comprising at least one fluid pump connectable to a detachable extracorporeal blood circuit, at least one pressure sensor monitoring pressure in a blood line of the blood circuit, a controller regulating the at least one fluid pump according to stored control settings and inputs for the at least one pressure sensor and a user interface, said method comprising:

a. displaying on the user interface a plurality of control settings which may be manually selected by an operator;

b. selecting a first independent control setting of the plurality of control settings;
c. adjusting the first independent control setting to a first independent control setting level selected by an operator;
d. temporarily storing the first independent control setting level, without implementing the first independent control setting level to control the device;
e. automatically establishing a limit for a first dependent control setting level based upon the first independent control level, without first implementing the first independent or first dependent control setting level to control the device, wherein the first independent control setting is a blood pressure limit of blood flowing through the circuit, the first dependent control setting is a filtrate pressure limit of filtrate flowing from a blood filter in the circuit and the first dependent control setting is limited to a predefined portion of the adjusted independent control setting level;
f. selecting first dependent control level for manual adjustment, wherein the selection converts the first dependent control setting to a second independent control setting and converts the first independent control setting to a second dependent control setting;
g. adjusting the second independent control setting to an second independent control setting level selected by an operator;
h. temporarily storing the second independent control setting level, without implementing the second independent control setting level to control the device;
i. automatically establishing a limit for the second dependent control setting level based upon the first independent control level, without first implementing the second independent control setting level or the second dependent control setting levels to control the device, and
j. implementing both the second independent control setting level and the second dependent control setting level to control the device by actuating a batch setting acceptance operation.

* * * * *